United States Patent
Kim

(10) Patent No.: US 6,485,302 B2
(45) Date of Patent: Nov. 26, 2002

(54) DENTAL ARTICULATOR

(75) Inventor: Yunsoon Kim, East Hartford, CT (US)

(73) Assignee: Nu-tek Dental, LLC, East Windsor, CT (US)

( * ) Notice: Subject to any disclaimer, the term of this patent is extended or adjusted under 35 U.S.C. 154(b) by 0 days.

(21) Appl. No.: 09/964,482

(22) Filed: Sep. 28, 2001

(65) Prior Publication Data

US 2002/0009689 A1 Jan. 24, 2002

Related U.S. Application Data

(62) Division of application No. 09/287,133, filed on Apr. 7, 1999.

(51) Int. Cl.[7] .............................................. A61C 19/00
(52) U.S. Cl. .............................. 433/74; 433/60; 433/64
(58) Field of Search .............................. 433/54, 57, 60, 433/61, 62, 64, 66, 67, 45, 50, 53

(56) References Cited

U.S. PATENT DOCUMENTS

| 981,430 A | 1/1911 | Kennedy |
| 1,736,006 A | 11/1929 | Hagman |

(List continued on next page.)

OTHER PUBLICATIONS

"Vertex Articulating System Instructions" (Pamphlet), Ceramco, pp. 1–8, Burlington, New Jersey, U.S.A.; Weybridge, Surrey, United Kingdom, 1997.

"Artiquick System Instructions for Use", Dental Ventures of America, Inc., Corona, California, U.S.A.

"Just Wing It Articulators", instructional handout.

"Die–Maker W.O.O. Articulator Instructions".

"Catalog of Articulators", LMT, pp. 29–36, Apr. 1994.

"Ballox Instructions", Shebah Dental Products, Inc., La Habra, California, U.S.A.

*Primary Examiner*—Ralph A. Lewis
(74) *Attorney, Agent, or Firm*—Birch, Stewart, Kolasch & Birch, LLP

(57) ABSTRACT

A dental modeling system includes a pair of supports for opposing dental casts which are articulated together by a pair of pivotally connected articulator arms. The support may include a plurality of integral registration pins extending from a top surface and a plurality of holes located in the top surface, which provide superior registration of a dental casts located thereon. The support may be directly attached to the articulator arm, or may be attached via a ball-and-socket joint, which, once located in the proper position, is glued in place. The articulator arm permits the castings to move toward and away from one another, and permits the replication of centric, excursive, and protrusive movements of the jaw. An alternative support for a dental cast includes a back member and a bottom member oriented at approximately 90° with respect to one another to form an L-shaped main body, onto which a dental cast may be attached. An auxiliary support member may be utilized onto which the dental casting is formed, and which is positionable on the support member and readily removable therefrom.

19 Claims, 10 Drawing Sheets

U.S. PATENT DOCUMENTS

| | | |
|---|---|---|
| 2,619,725 A | 12/1952 | Roeser |
| 2,786,272 A | 3/1957 | Lindley |
| 3,937,773 A | 2/1976 | Huffman |
| 3,965,576 A | 6/1976 | Eveliand |
| 4,021,916 A | 5/1977 | Spalten |
| 4,022,419 A | 5/1977 | Haker |
| 4,163,319 A | 8/1979 | Ouaknine |
| 4,265,619 A | 5/1981 | Lucki et al. |
| 4,273,533 A * | 6/1981 | Della Croce ................. 433/55 |
| 4,382,787 A | 5/1983 | Huffman |
| 4,398,884 A | 8/1983 | Huffman |
| 4,439,151 A | 3/1984 | Whelan |
| 4,449,930 A | 5/1984 | Huffman |
| 4,449,931 A | 5/1984 | Saito |
| 4,451,234 A | 5/1984 | Oye |
| 4,481,162 A | 11/1984 | Huffman |
| 4,508,506 A | 4/1985 | Jackson |
| 4,533,323 A | 8/1985 | Huffman |
| 4,538,987 A | 9/1985 | Weissman |
| 4,548,581 A | 10/1985 | Huffman |
| 4,608,016 A | 8/1986 | Zeiser |
| 4,708,648 A | 11/1987 | Weissman |
| 4,721,464 A | 1/1988 | Roden et al. |
| 4,734,033 A | 3/1988 | Huffman |
| 4,767,330 A | 8/1988 | Burger |
| 4,786,253 A | 11/1988 | Morais |
| 4,842,242 A | 6/1989 | Huffman |
| 4,842,515 A | 6/1989 | Zeiser |
| 4,957,435 A | 9/1990 | Jinoian et al. |
| 5,129,822 A | 7/1992 | Dobbs |
| 5,197,874 A | 3/1993 | Silva et al. |
| 5,232,365 A | 8/1993 | Ikehara |
| 5,286,191 A | 2/1994 | Poveromo |
| 5,306,145 A | 4/1994 | Michael |
| 5,360,337 A | 11/1994 | Westdyk |
| 5,403,185 A | 4/1995 | Presswood |
| 5,425,636 A | 6/1995 | Ghim |
| 5,466,152 A | 11/1995 | Walter |
| 5,506,095 A | 4/1996 | Callne |
| 5,575,899 A | 11/1996 | Huffman |
| 5,622,497 A | 4/1997 | Cho |
| 5,658,143 A | 8/1997 | Kuperman |
| 5,766,007 A | 6/1998 | Huffman |
| 5,769,634 A | 6/1998 | Choi |
| 5,788,489 A | 8/1998 | Huffman |
| 5,807,102 A | 9/1998 | Lang et al. |
| 5,846,076 A | 12/1998 | Garland |
| 5,957,688 A | 9/1999 | Van Valey |
| 6,089,863 A | 7/2000 | Van Valey |
| 6,106,284 A | 8/2000 | Cronin et al. |
| D430,672 S | 9/2000 | Huffman |
| 6,318,999 B1 * | 11/2001 | Kim ............................ 433/74 |

* cited by examiner

DENTAL ARTICULATOR

This application is a divisional of co-pending application Ser. No. 09/287,133, filed on Apr. 7, 1999, the entire contents of which are hereby incorporated by reference and for which priority is claimed under 35 U.S.C. §120.

BACKGROUND OF THE INVENTION

1. Field of the Invention

The present invention relates to a dental articulator which permits a pair of opposing dental casts to be repeatedly positioned adjacent one another and moved away from one another for the preparation of dental prosthesis elements such as crowns, bridges, caps, etc. More particularly, the present invention is directed to a dental modeling system including supports for dental casts, and to an inexpensively formed articulator which permits replication of centric, excursion and protrusive movements while still allowing proper registration of the maxillary and mandibular dental casts.

2. Background of the Invention

Various dental articulators are known in the art to which a pair of dental casts are mounted which simulate the movement of the human jaw. Typically, dental articulators are utilized by dentists or dental technicians to create an accurately fitting dental prosthesis, such as a crown, bridge, or cap. Dental articulators are used to mount castings of a patient's teeth which are used as a model for the creation of the dental prosthesis. In preparing the dental casts, a dentist normally makes a negative impression of the patient's teeth, which may be a partial or full arch impression. This negative impression serves as a mold for developing a casting of the patient's teeth. The negative impression is filled with a pourable casting stone which is allowed to harden and thereby form a replica of the patient's teeth. The upper and lower castings may then be attached to an articulator which allows the opposing casts to be moved toward or away from one another.

Typically, the dental technician will be working on one tooth or several teeth in one of the dental casts. Therefore, it is necessary for the dental technician to separate the tooth from the rest of the dental cast. This separation is performed by sawing through the casting on opposite sides of the tooth. However, doing so separates the tooth from the remainder of the casting which creates a problem when repositioning the tooth with respect to the remainder of the dental cast. In order to perform such repositioning, previous methods have been developed whereby one or more pins are inserted into a lower surface of the portion of the dental cast containing the single tooth, and corresponding holes are placed in the base of the remaining portion of the dental cast. However, the requirement for the provision of pins and holes requires additional labor, thereby increasing costs and slowing the process. Further, this method does not necessarily lead to an accurate re-registration of the single tooth with respect to the remaining portion of the dental cast. This technique wherein the model is poured, allowed to harden, then cut into dies, and is then pindexed into another base is known as "a dry pinning technique."

Another method known as "a wet pinning technique" utilizes a tray support member having a plurality of holes therein into which several indexing pins are placed. The tray support member and the indexing pins are then covered with casting material which is either poured directly onto the tray support member, or alternatively, into the negative impression taken by the dentist. The negative impression is then placed over the tray support member and allowed to harden. Once the casting material is hardened, the hardened casting material may be removed from the tray support member with the indexing pins being retained in the casting material. The model may be cut into segmented pieces and returned to the tray support member by placing the segmented portions with their indexing pins back into the indexing holes from which they were taken. The castings or tray support members may be attached to articulator arms for moving the castings toward and away from one another. However, present commercially available articulators for wet pinning systems are flimsy and do not permit reliable registration of the upper and lower castings with respect to one another. Also, the tray support member onto which the casting stone is poured does not allow positive, accurate, and solid re-registration of a segmented tooth onto the tray support member, thus resulting in improper spatial relationship of the segmented tooth with respect to the remainder of the dental cast, which can result in the formation of an improperly fitting crown, cap, or bridge. Correcting such an improperly fitting dental prosthesis unnecessarily increases the amount of labor, costs, material, and patient's time in the office or lab.

There is a need in the art for a simple dental articulator which allows better stabilization of the prosthesis element being worked on, without shifting, or movement of the prosthesis dies in the lab while being worked on. There is also a need in the art for a dental articulator which provides accurate registration of the mandibular and maxillary quadrants or arches of a patient's mouth, while also permitting recreation of the jaw movements of the patient in centric, excursive, and protrusive manners.

The current invention addresses the dichotomy of the "dry pinning" vs. wet pinning technique. Historically the dry pinning technique has been accurate but very labor intensive and time consuming. Conversely, the wet pinning technique has been less labor intensive but not as accurate. The current invention addresses both. The truncated pyramids and the tapered and appropriately sized holes, (pins optional) make for an extremely accurate repositioning of the casts. The elimination of separate casts and the need for time consuming pindexing is elminated.

Another object of the present invention is to provide a dental modeling system which permits the castings to be produced and articulated in the most economical fashion, both in cost and time required to produce an articulated model of a patient's teeth. Another problem addressed and solved is that of using quickly setting cyanoacrylate glue. The glue slot and glue hole of the invention prevent unnecessary glue from flowing into and onto undesired areas, and therefore reduces the need for cleanup. In particular, skin contact with the glue is prevented.

SUMMARY OF THE INVENTION

The above and other objects of the present invention are obtained by a dental modeling system comprising a support for a dental cast, the support including a main body having a top surface and a bottom surface, a plurality of pyramidal shaped registration pins formed integrally with the main body as a one-piece unit and extending upwardly from the top surface of the main body, a plurality of tapered holes located in the top surface of the main body and extending therein, and at least one registration groove formed in the top surface of the main body. This and another support may be attached to an articulator including a first articulator arm having a first hinged portion, a second articulator arm having a second hinged portion pivotally connected to the first hinged portion of the first articulator arm, with one support attached to the first articulator arm for supporting a first dental cast and a second support attached to the second articulator arm for supporting a second dental cast. This support may be used as part of a wet pinning system as described above wherein the casting stone is placed on the support while in the viscous state and allowed to harden on the support.

The articulator of the present invention may be utilized with previously formed and hardened casts (available by different manufacturers) by utilizing an alternative support including a back member and a bottom member which together form an L-shaped main body, with the back member being oriented at approximately 90° with respect to the bottom member. The support may be fastened to the previously formed and hardened dental cast by using an appropriate fastener, such as cryanoacrylic glue. Alternatively, the casting may be formed directly onto the L-shaped main body portion, for example, in instances where it will not be necessary to segment the casting into separate elements.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
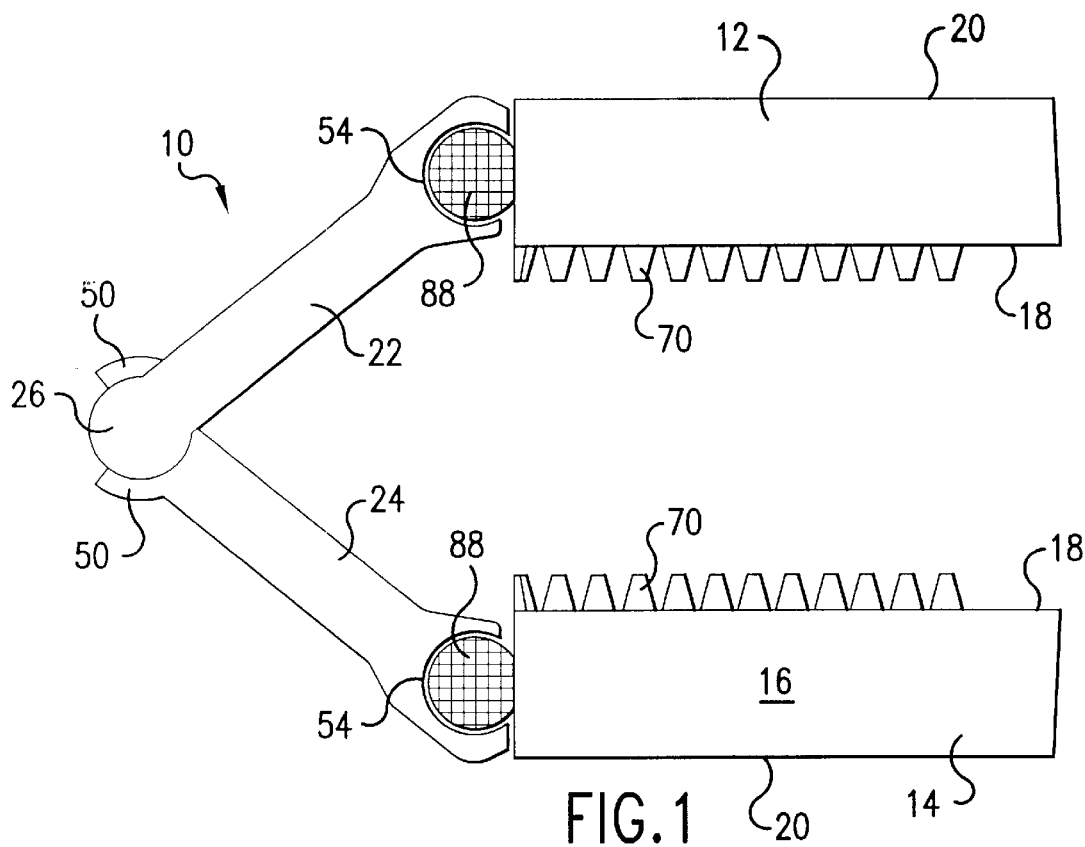
FIG. 1 is a side view of the dental articulator according to a first embodiment.
Figure 26:
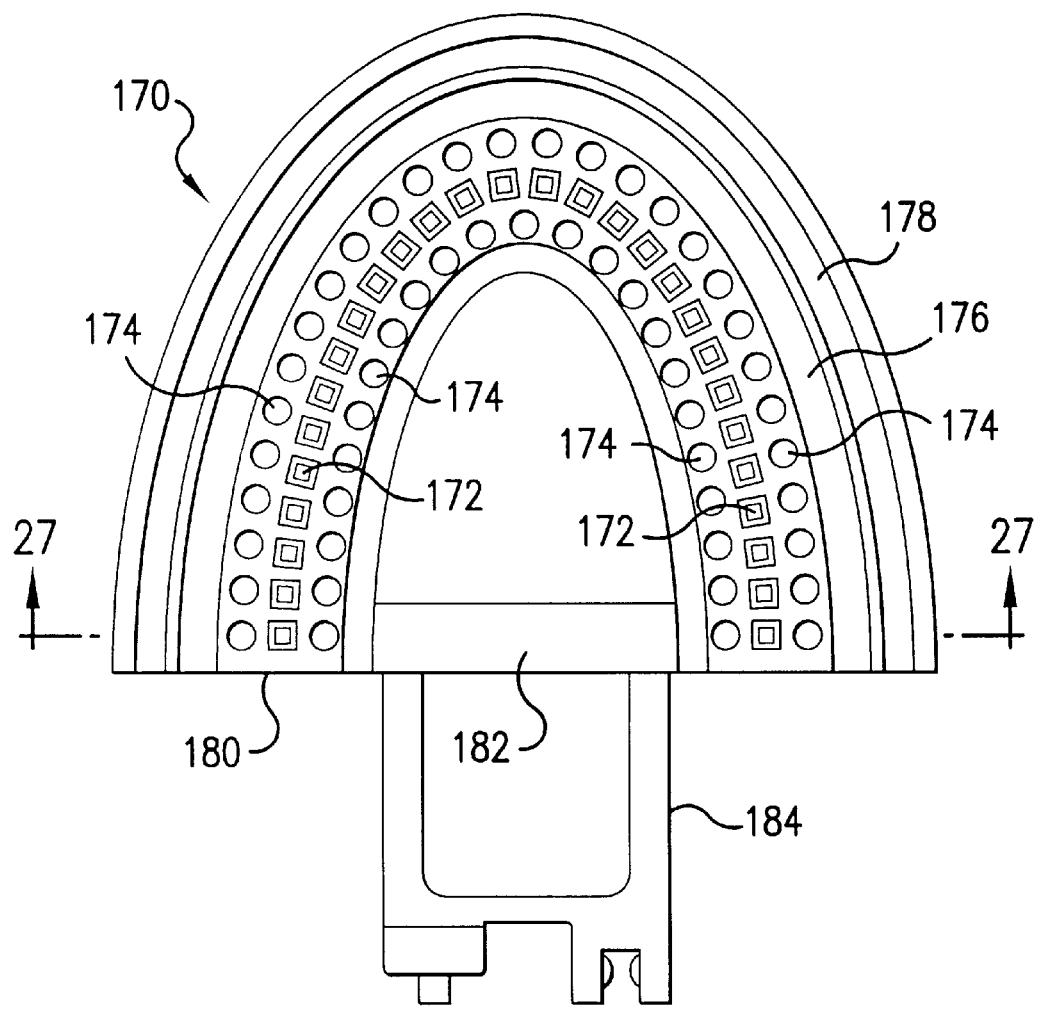
FIG. 26 is a plan view of a full-arch support of the present invention.
Figure 27:
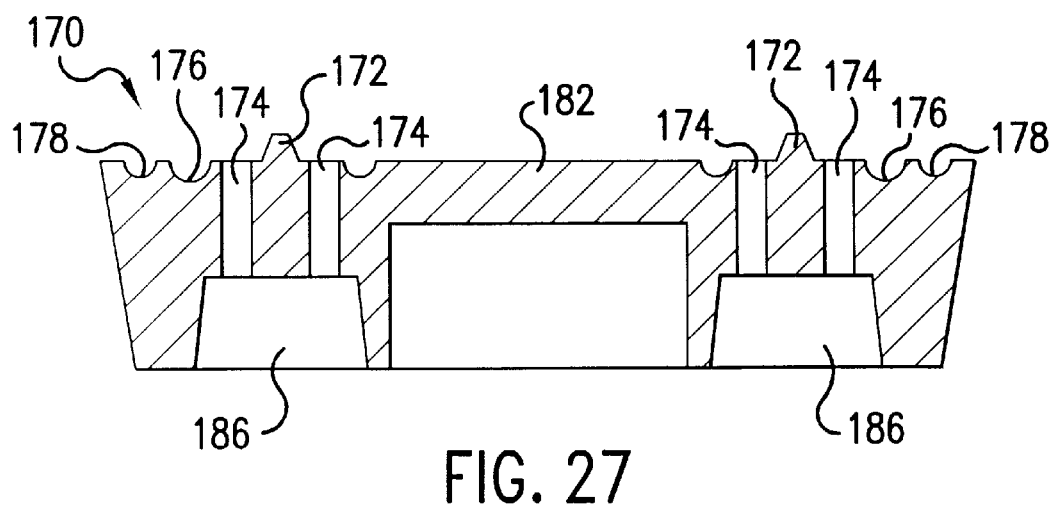
FIG. 27 is a cross-sectional view taken along lines 27—27, in FIG. 26.

A dental modeling system 10 according to the present invention will now be described with reference to FIGS. 1–27. FIG. 1 shows a first embodiment of the dental modeling system 10. In the first embodiment, an upper support 12 is arranged in an opposing relationship with respect to a lower support 14. Although the upper support 12 and lower support 14 are shown as quadrants in most of the Figures, it should be understood that full arches may be utilized as shown in FIGS. 26 and 27. In FIG. 1, the upper support 12 is identical to the lower support 14, and therefore, discussion will be made with respect to the lower support 14 with the understanding that the same description applies to the upper support 12. The lower support 14 includes a main body 16 which has a block-like external configuration. The main body 16 has an upper surface 18 and a lower surface 20. The upper surface 18 is configured to support a dental cast C thereon. A more detailed discussion of the lower support 14 will follow.

The upper support 12 is attached to a first articulator arm 22, and the lower support 14 is attached to a second articulator arm 24. The first articulator arm 22 and the second articulator arm 24 are pivotally interconnected together by a hinge 26. The hinge 26 allows the first articulator arm 22 to pivot with respect to the second articulator arm 24, thus causing the upper support 12 to be movable toward and away from the lower support 14. Thus, with a dental cast C attached to both the upper support 12 and the lower support 14, it is possible to simulate the opening and closing movement of a patient's teeth with the dental modeling system 10.

The articulator arms of the present invention will now be described in detail, with particular reference to FIGS. 2–6. The first articulator arm 22 is identical to the second articulator arm 24. Thus, the production of only one articulator arm is necessary for use with the dental modeling system 10 of the present invention. The following description will be made with respect to the first articulator arm 22, with the understanding that the same description applies to the second articulator arm 24. The first articulator arm 22 includes a pair of spaced apart arms 28. One end of each of the arms 28 is connected to a first cross-member 30 and the other end of each of the arms 28 is connected to a second cross-member 32. The arms 28 have a cross-section wherein the height (as viewed in FIG. 3) is approximately twice as large as the width (as viewed in FIG. 4). This permits the articulator arm 22 to be more susceptible to favorable lateral deflection (as viewed in FIG. 4) than unfavorable vertical deflection (as viewed in FIG. 3).

Figure 4:
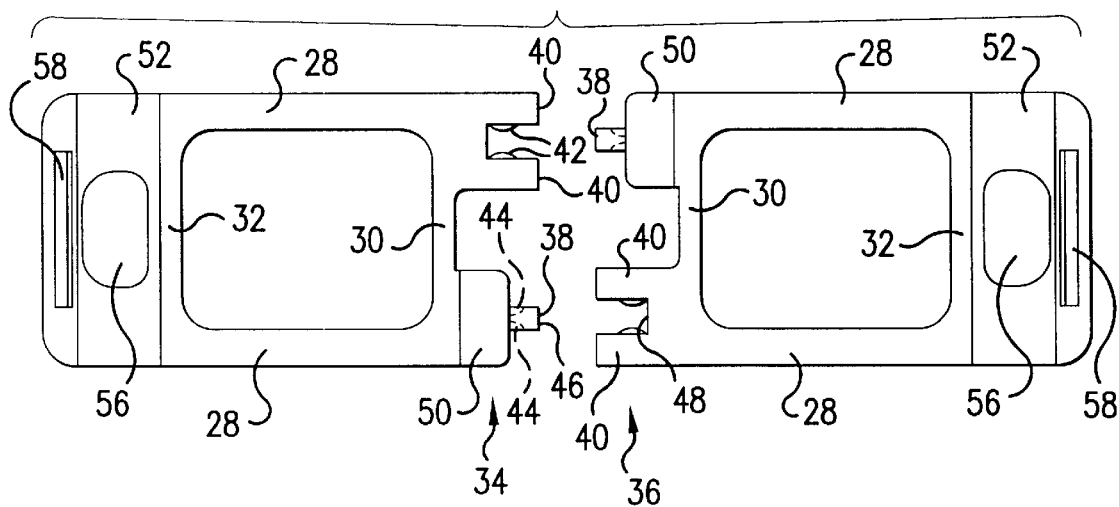
FIG. 4 is an exploded plan view of a pair of articulator arms of the present invention.
Figure 5:
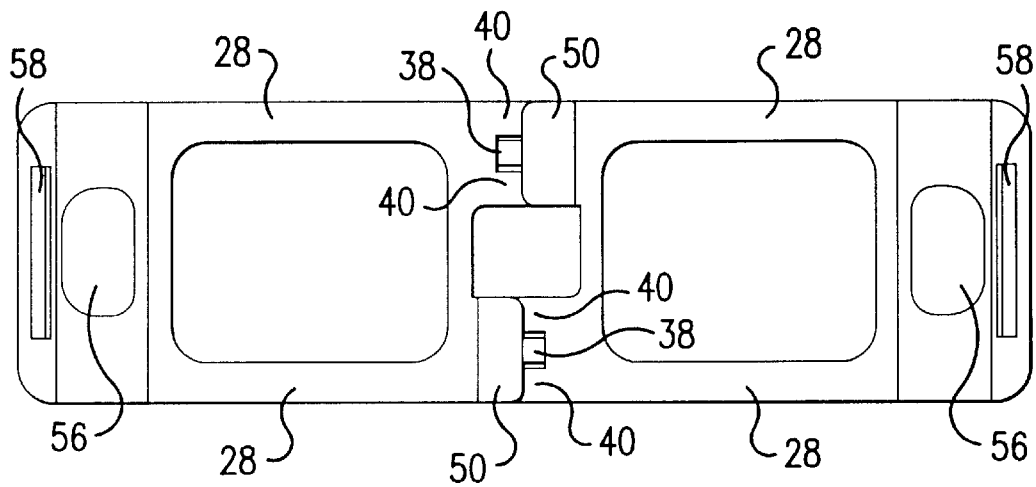
FIG. 5 is a plan view of the pair of articulator arms attached together.
Figure 6:
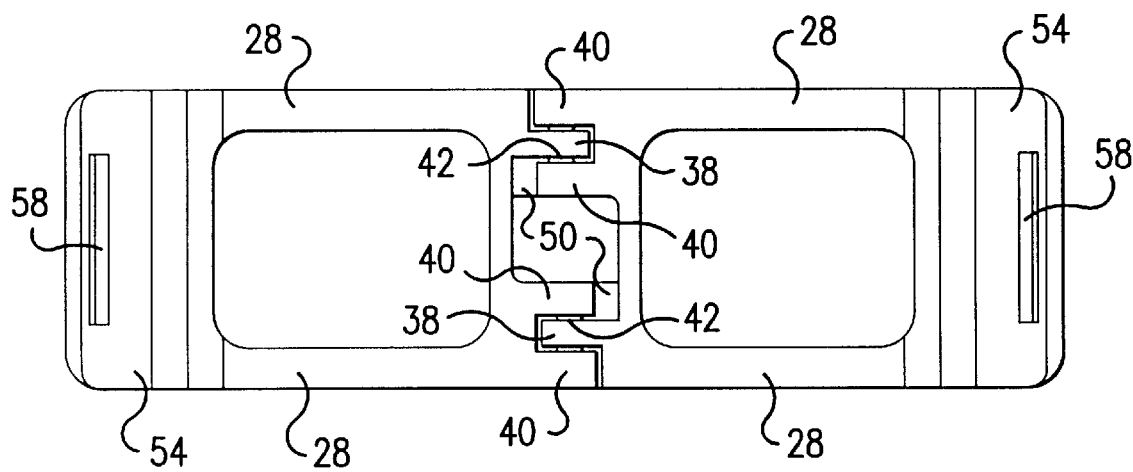
FIG. 6 is a bottom view of the pair of articulator arms in an assembled condition.

The cross-member 30 of the first articulator 22 supports a first hinge portion 34. Accordingly, the second articulator arm 24 supports a second hinge portion 36 which may be matingly engaged with the first hinge portion 34 to form the hinge 26. The first hinge portion 34 includes a first finger 38 extending from the cross-member 30 near one end thereof. A pair of second fingers 40 extend from the first cross-member 30 adjacent the other end thereof. As can be seen in FIGS. 4 and 6, the first fingers 38 of one articulator arm are insertable between the second fingers 40 of the other articulator arm.

Each of the second fingers 40 includes a projection 42 extending therefrom in a direction toward the opposing second finger 40. Each of the first fingers 38 include a pair of dimples 44, with one dimple 44 being formed on each side of the first finger 38. The dimples 44 are shaped to correspond with the profile of the projections 42. When the first articulator arm 22 is assembled with the second articulator arm, the projections 42 of the second fingers 40 of the first articulator arm 22 are located within the dimples 44 of the first finger 38 of the second articulator arm 24. Similarly, the projections 42 of the second fingers 40 of the second articulator arm 24 are located in the dimples 44 of the first finger 38 of the first articulator arm 22. The first articulator arm is pivotable with respect to the second articulator arm 24 about a pivot axis defined by a line drawn through the centers of the aligned projections 42 and dimples 44.

Each of the first fingers 38 includes an introduction area 45 surrounding the dimples 44. Thus, when the first articulator arm 22 is partially assembled with the second articulator arm 24, the projections 42 may slide along the introduction area 45 surrounding the dimples 44. Thus, although the projections 42 may not be properly seated in the dimples 44, the projections 42, and thus the second fingers 20, are nonetheless held in position by the frictional forces between the projections 42 and the introduction area 45. Also, as the first articulator arm is being assembled with the second articulator arm 24, and the first finger 38 is being inserted between the second fingers 40, a gap between the second fingers 40 increases slightly to allow the first finger 38 to slide past the projections 42 until the projections 42 are properly seated in the dimples 44, at which time the second fingers move back to their original position because of the elasticity of the material from which the articulator arms are formed. Preferably, the material forming the articulator arms is a thermoplastic material, although other suitable materials may be utilized.

When the dental modeling system 10 is formed as shown in FIG. 1, the hinge 26 permits movement of the upper support 12 with respect to the lower support 14 to simulate the three movements of the human jaw, those being centric, protrusive and excursion, by appropriately pivoting the hinge about the interconnection between the projections 42 and the dimples 44, or by shifting the projections 42 out of the dimples 44 and moving them along the introduction areas 45.

The first cross-member 30 is generally parallel with the second cross-member 32, and both the first and second cross members 30, 32 extend generally perpendicular to the pair of arms 28.

Figure 3:
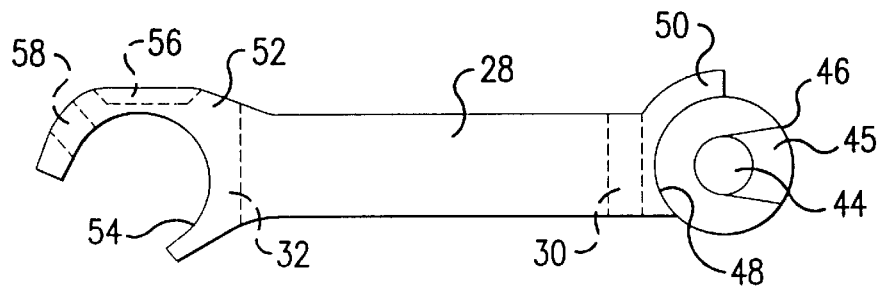
FIG. 3 is a side view of an articulator arm of the present invention.

As shown in FIG. 3, end portions 46 of each of the first and second fingers 38, 40 have a circular profile which is received in a correspondingly shaped recess 48. As the first articulator arm 22 pivots with respect to the second articulator arm 24 about the hinge 26, the end portions 46 of the fingers slide along the recesses 48, thereby providing a well-defined movement with high strength. However, it should be understood that the articulator arms 22, 24 may be configured such that sliding does not occur between the end portions 46 and the recesses 48, but rather a clearance is provided therebetween. To increase the area of the recesses 48, a wing 50 is provided which extends outwardly from the first cross-member 30, as shown in FIGS. 3 and 4. This provides a resistance to compression forces between mounted maxillary and mandibular casts, especially when there are multiple missing teeth.

The second cross-member 32 supports a socket member 52 which receives and supports an appropriately shaped attachment member of a support, such as the upper support 12. The interior surface of the socket member 52 is formed as an elongated part-cylindrical surface 54. The outer surface of the socket member 52 includes a depression 56 therein for receiving a finger or thumb of a user. In addition, a glue slot 58 is provided in the socket member 52 which penetrates from the outer surface to the elongated part-cylindrical surface 54. The part-cylindrical surface 54 of the socket member 52 is formed as an arch as shown in FIG. 3 which traverses more than 180° so that a cylindrical or spherical element placed into the socket member 52 will be retained thereby. The articulator arm 22 is formed of a thermoplastic material, and thus the opening of the socket member 52 may increase slightly as an attachment member is inserted thereinto, and may return to its original shape shown in FIG. 3 to thereby retain the attachment member in the socket member 52.

Figure 2:
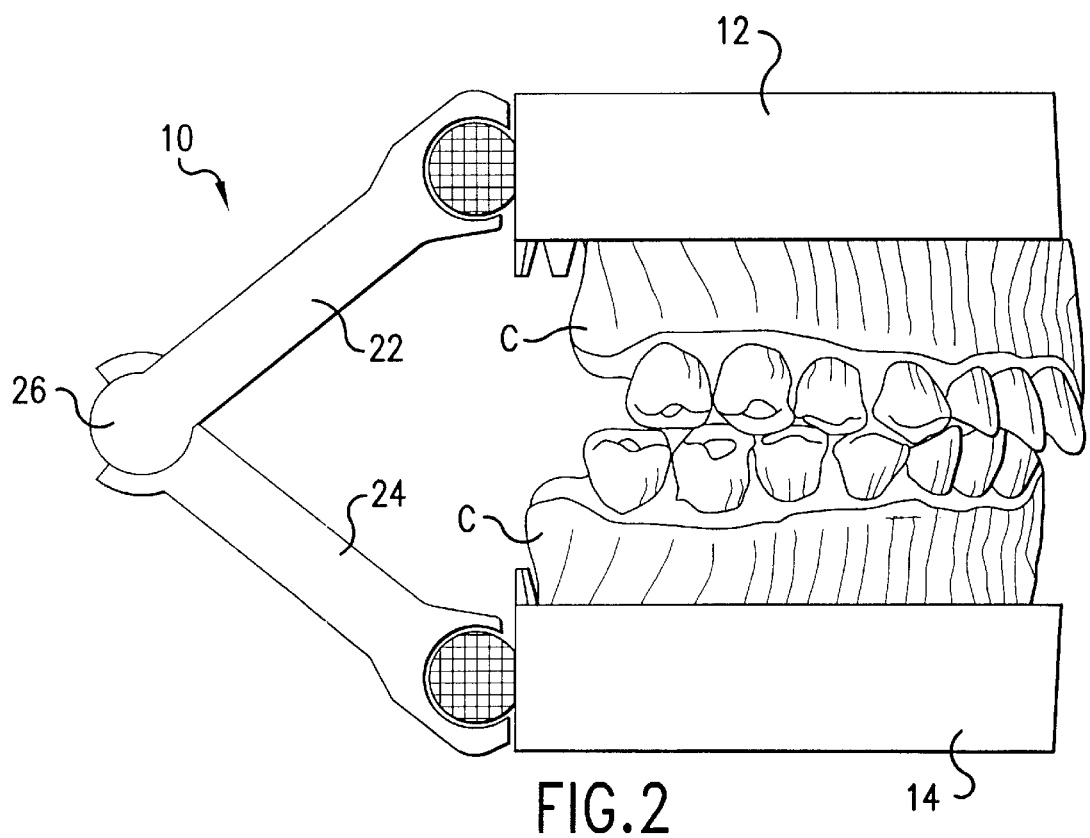
FIG. 2 is a side view of the dental articulator shown in FIG. 1, and having dental casts attached thereto.

When the first articulator arm 22 is assembled with the second articulator arm 24, the articulator arms 22, 24 are pivotable about the hinge 26 until a point is reached wherein portions of the articulators arms 22, 24 adjacent to the first cross-members 30 engage one another, thereby preventing further closing movement of the articulator arms. Such a stop position is shown in FIG. 2, for example.

The lower support 14 will now be described in detail with particular reference to FIGS. 7–11. The upper surface 18 of the lower support 14 includes a plurality of registration pins 70 extending upwardly from the upper surface 18. The registration pins are evenly spaced apart and aligned in a row extending centrally along the upper surface 18 of the main body 16. However, the lower support 14 may be configured such that the registration pins 70 are unevenly spaced apart, or may be arranged in more than one row, or a row not extending along the center of the main body 16. The registration pins are tapered inwardly in a direction proceeding away from the upper surface. Preferably, the registration pins 70 are formed as pyramidal elements with the top portion thereof removed to form truncated pyramids. Located on each side of the registration pins 70 are two rows of holes 72. The holes 72 are also evenly spaced and arranged in rows extending parallel to the row of registration pins 70. However, other arrangements of the holes may be made other than the two parallel rows of evenly spaced holes, as set forth herein. The holes are circular in cross-section and taper inwardly extending into the main body 16 from the upper surface 18.

Located outwardly of the holes 72 are a first groove 74 and a second groove 76. The first groove is formed by a pair of straight first groove portions 74a extending parallel to the rows of holes 72 and registration pins 70. One end of each of the straight first groove portions 74a terminates at the rear wall 78 of the main body 16, and the other ends of the straight first groove portions 74a are interconnected by a semi-circular curved first groove portion 74b. Similarly, the second groove is formed by a pair of straight second groove portions 76a extending parallel to the straight first groove portion 74a and outwardly thereof. One end of the straight second groove portion 76a terminates at the rear wall 78, and the other ends of the straight second groove portions 76a are interconnected by a semi-circular curved second groove portion 76b. Except for the presence of the registration pins 70 extending upwardly from the upper surface 18, and the presence of the first and second grooves 74, 76 extending into the main body 16, the upper surface 18 is essentially flat and forms a stable planar base for receiving casting stone material thereon for forming a dental cast C.

Figure 7:
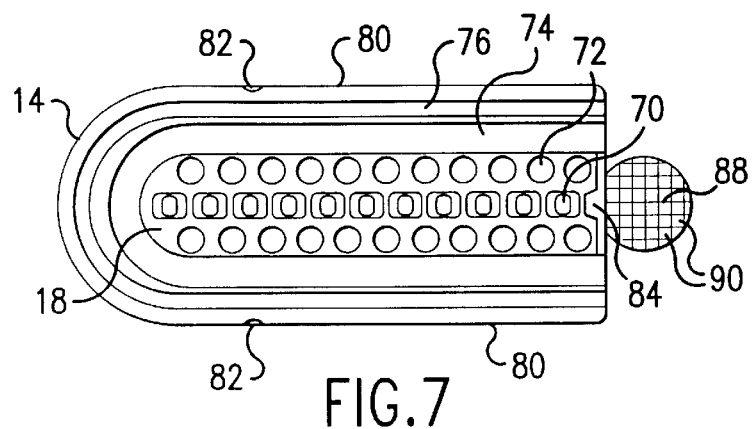
FIG. 7 is a top view of a support for a dental cast according to a first embodiment of the invention.
Figure 8:
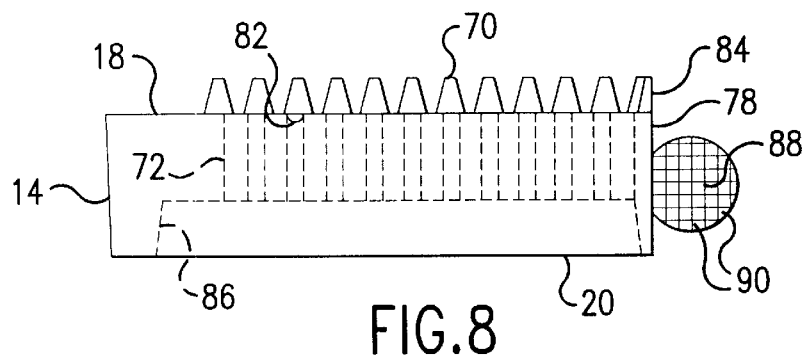
FIG. 8 is a side view of the support shown in FIG. 7.

As shown in FIG. 7, the first groove 74 is wider and deeper than the second groove 76, although equally sized grooves may be utilized. Although the grooves 74, 76 are continuous from one end to another, the grooves may also be configured as segmented discontinuous groove segments.

Extending between the upper surface 18 and the lower surface 20 are side walls 80. As evident from FIGS. 10 and 11, the side walls are tapered slightly inwardly from the upper surface 18 to the lower surface 20. This tapering of the side walls 80 permits the removal of excess stone material from the dental cast C by utilizing a grinding wheel without causing damage to the entire side wall 18 of the lower support 14. Instead, the excess stone may be ground away until only the uppermost portion of the side wall 80 engages the grinding wheel.

A pair of notches 82 are located in the upper portion of the side walls 80 adjacent the upper surface 18, which are utilized to identify the approximate location of the cuspids of the dental cast C. Also, the notches 82 provide a convenient entry point for a tool, such as a screwdriver, which may be inserted into the notch to pry the dental cast C off of the upper surface 18 of the lower support 14. Further, to ease the separation of the dental cast C from the lower support 14, the upper surface 18 may be coated with silicone or an oil based spray which acts as a separating medium for removing the dental cast C from the upper surface 18 of the lower support 14.

In order to prevent the unhardened casting stone from sliding off of the upper surface 18 and onto the rear wall 78, a blocking member 84 is provided which extends upwardly from the upper surface 18 adjacent the rearmost registration pin 70.

Figure 9:
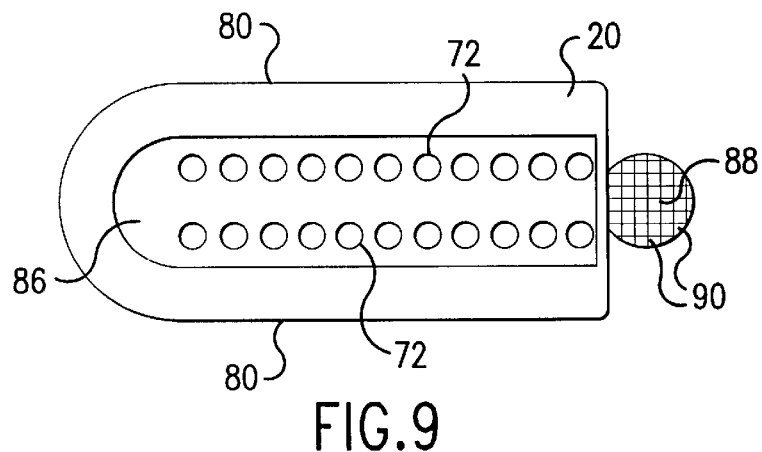
FIG. 9 is a bottom view of the support shown in FIG. 7.
Figure 10:
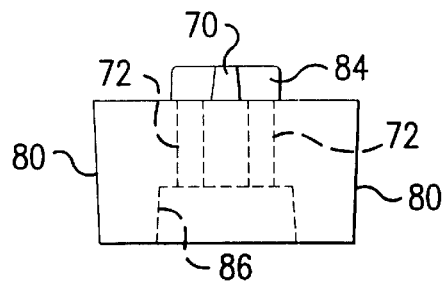
FIG. 10 is a front end view of the support shown in FIG. 7.
Figure 11:
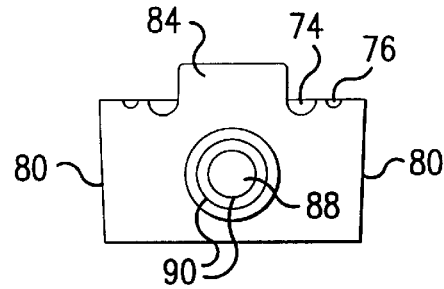
FIG. 11 is a rear end view of the support shown in FIG. 7.

The lower surface 20 of the main body 16 includes a cavity 86 therein. The holes 72 extend through the main body 16 and terminate with openings in the cavity 86 as shown in FIG. 9. The rear wall 78 of the main body 16 includes an attachment ball 88 thereon. The attachment ball 88 is formed of a part spherical member connected to the rear wall 78. The attachment ball 88 includes a plurality of grooves 90 extending into the surface of the attachment ball 88. The grooves extend either partially or fully circumferentially around each attachment ball, and the grooves 90 may intersect with one another. When the attachment ball 88 is inserted into the elongated part-cylindrical surface 54 of the socket member 52 as shown in FIG. 2, glue is applied to the junction between the attachment ball 88 and the cylindrical surface 54. The glue slot 58 and the socket member 52 permits the glue to be inserted more readily into the interior junction between the attachment ball 88 and the cylindrical surface 54. Further, the depression 56 permits a user applying the glue to firmly hold the articulator arm 22 without the glue contacting the users finger. The grooves 90 in the attachment ball 88 permit the glue to flow along the attachment ball by capillary action or wicking action, thereby promoting the flow of adhesive along the entire junction, thereby resulting in a superior bond.

As used herein, the plurality of grooves formed in a surface which permits the flow of adhesive thereinto and therealong is termed "glue mesh".

Figure 12:
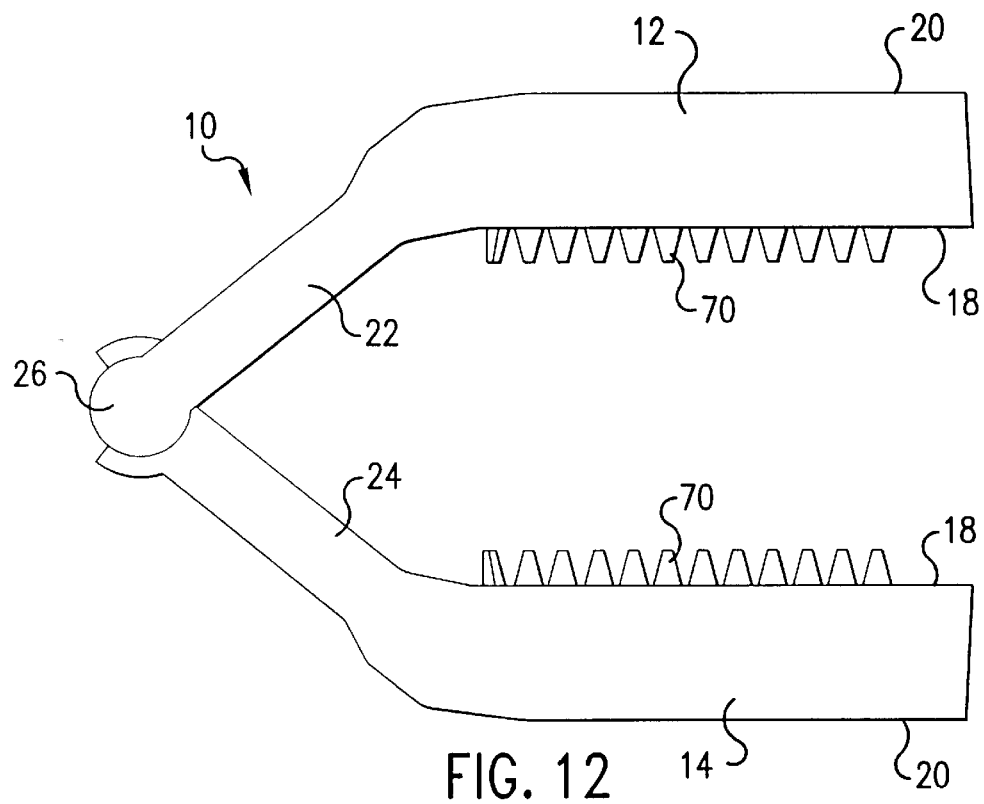
FIG. 12 is a dental articulator according to a second embodiment of the present invention.
Figure 13:
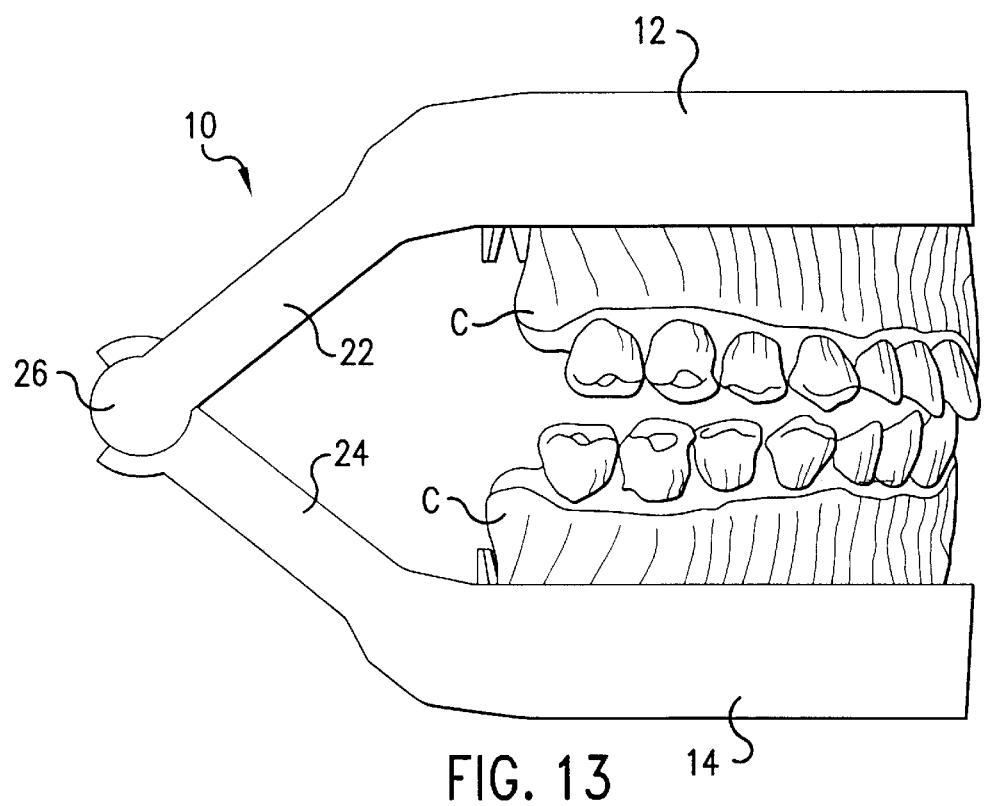
FIG. 13 is a side view of the dental articulator shown in FIG. 12 with dental casts attached thereto.
Figure 14:
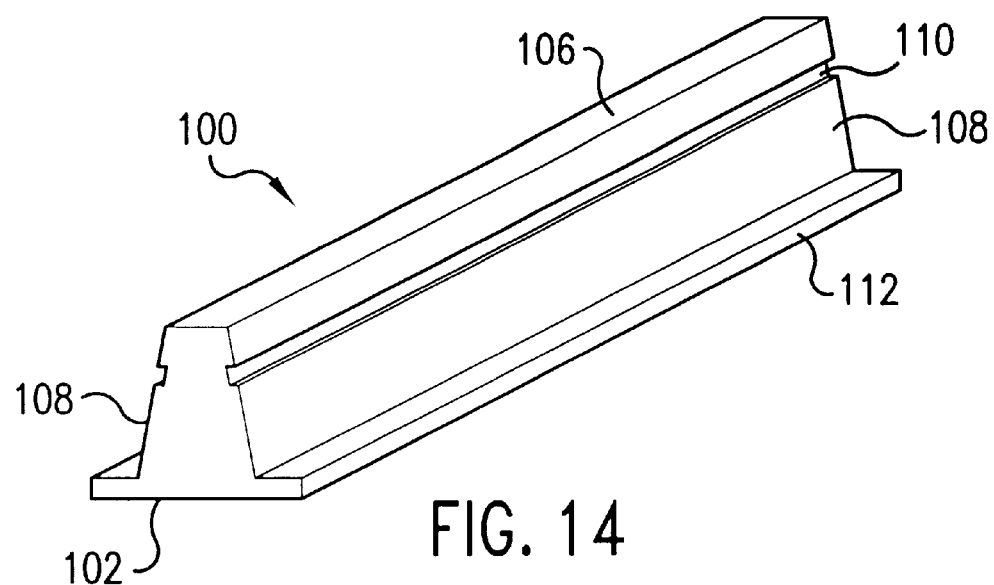
FIG. 14 is a perspective view of an auxiliary support member, or auxiliary cap, of the present invention.
Figure 15:
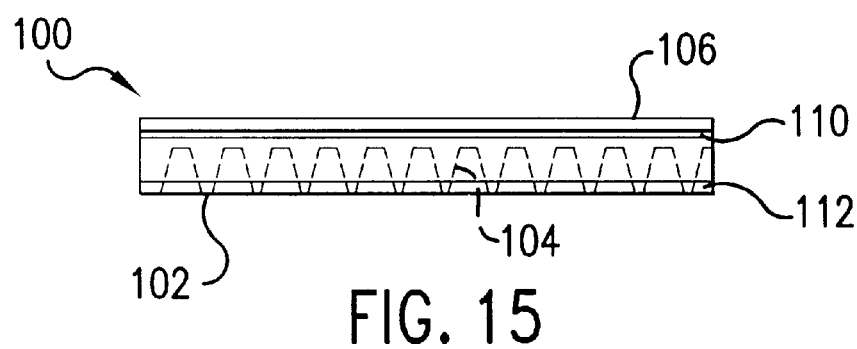
FIG. 15 is a side view of the auxiliary cap of the present invention.
Figure 16:
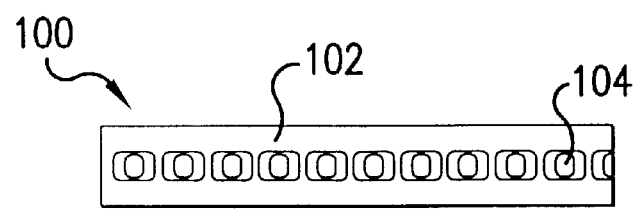
FIG. 16 is a bottom plan view of the auxiliary cap of the present invention.

As shown in FIGS. 1 and 2, the upper and lower supports 12, 14 are attached to the first and second articulator arms 22, 24, respectively, utilizing the ball and socket arrangement which is held in position with glue, such as a fast acting cryanoacrylic glue. However, as shown in FIGS. 12 and 13, the upper and lower supports 12, 14 may be formed directly with the first and second articulator arms 22, 24, respectively, with each being a one-piece unitary member. This eliminates the necessity for the attachment ball 88 and the socket member 52, and thus eliminates the requirement for gluing.

In practice, casting stone may be placed on the upper surface 18 of the main body 16, and the negative impression of the patient's teeth taken the by the dentist may be pressed onto the casting stone. The main body 16 and the negative impression may be pressed toward one another so that the casting material flows into the negative impression and into the first and second grooves 74, 76 of the main body 16. At that time, a portion of the casting material will flow into the holes 72 which, when the casting material is removed from the upper surface 18, provides additional registration points between the dental cast C and the main body 16. Although the provision of the registration pins 70 provides sufficient registration of the dental cast C with respect to the main body 16, even if the dental cast is segmented into smaller portions comprising one or two teeth, the holes 72 provide an additional mechanism whereby a dental technician may insert one or more pins thereinto prior to placing the casting material onto the upper surface 18. Thus, when the dental cast C is separated from the main body 16, the pins are fixed to the dental cast C and can be reinserted into the holes 72 to provide additional registration elements between a dental cast C and the main body 16. Although the holes 72 are tapered, it should be understood that cylindrical holes may be utilized as well. However, the tapered holes 72 permit the use of a tapered pin which provides a very positive connection between the pin and the corresponding hole 72.

When a dental cast C is formed on the upper surface 18, it is possible to assist the separation of the dental cast C from the upper surface 18 by blowing air into the cavity 86 and through the holes 72. Alternatively the main body 16 may be pressed down onto an ejector block (not shown) having a plurality of ejector pins extending upwardly therefrom which pass through the holes 72 and against the bottom surface of the dental cast C. Further, as set forth above, a tool may be inserted between dental cast C and the upper surface 18, for example at the notch 82, to promote separation of the dental cast from the upper surface 18.

As shown in FIGS. 14–18, an auxiliary cap 100 may be utilized with the upper support 12 and/or the lower support 14. The auxiliary cap 100 is configured with a lower surface 102 which engages with the upper surface 18 of the main body 16. The lower surface 102 therefore includes a plurality of recesses 104 which are correspondingly shaped to receive the registration pins 70 of the main body 16. These recesses 104 cooperate with the registration pins 70 to provide a unique registration of the auxiliary cap 100 with respect to the main body 16.

Figure 17:
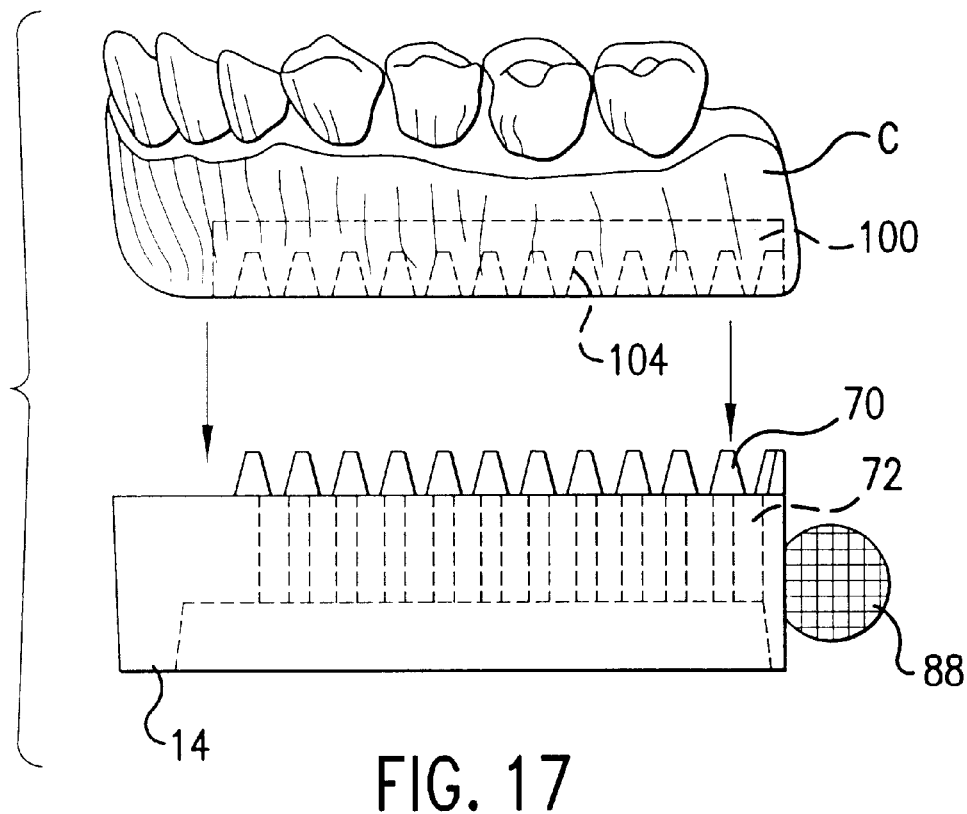
FIG. 17 is an exploded side view showing the auxiliary cap with a dental casting thereon being attached to the support member of the first embodiment.
Figure 18:
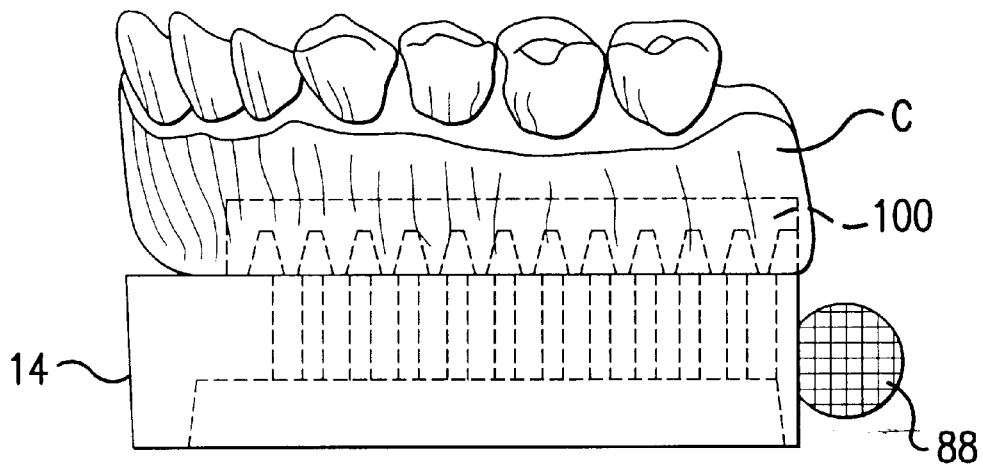
FIG. 18 is a side view showing the auxiliary cap attached to the support member of the first embodiment.

The auxiliary cap 100 has an upper surface 106 and a pair of opposing tapered sidewalls 108. The sidewalls 108 of the auxiliary cap 100 are tapered in the manner of the registration pins 70 of the main body 16. The sidewalls 108 include a pair of longitudinal grooves 110 therein. The grooves 110 act as interlocking mechanisms which promote the adhesion of the dental cast C thereonto which allows the casting material to flow thereinto and become essentially locked in place. A flange 112 is located at the bottom of the auxiliary cap 100 for engaging the upper surface 18 of the main body 16. In use, the casting stone is placed on the upper surface 106 of the auxiliary cap 100 instead of on the upper surface 18 of the main body 16. The dental cast C thereby formed is thus permanently affixed to the auxiliary cap 100 which may be removed from and reinserted onto the main body 16. Additionally, the auxiliary cap 100 may be cut into segments along with the dental cast C, and these segments are reliably repositionable onto the upper surface 18 of the main body 16 in proper registration with the remaining dental cast As shown in FIG. 17, the auxiliary cap 100 with the dental cast C formed thereon is locatable above the upper surface 18 of the main body, and is lowered thereon to a position shown in FIG. 18 wherein the registration pins 70 of the main body 16 are located within the recesses 104 of the auxiliary cap 100 to firmly and accurately retain the auxiliary cap 100 onto the main body 16 in a proper registrational relationship.

Figure 19:
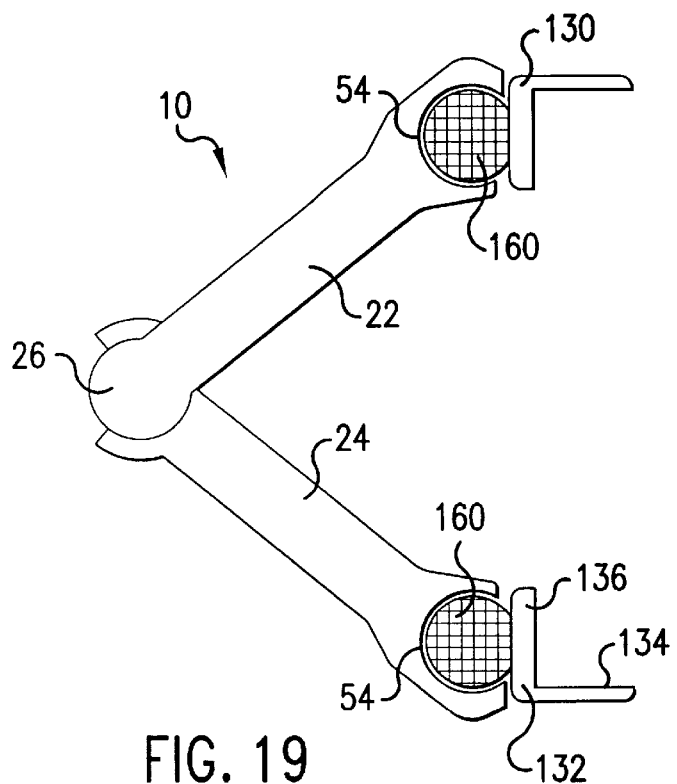
FIG. 19 is a side view of a dental articulator according to a third embodiment of the present invention utilizing a support according to a second embodiment.
Figure 20:
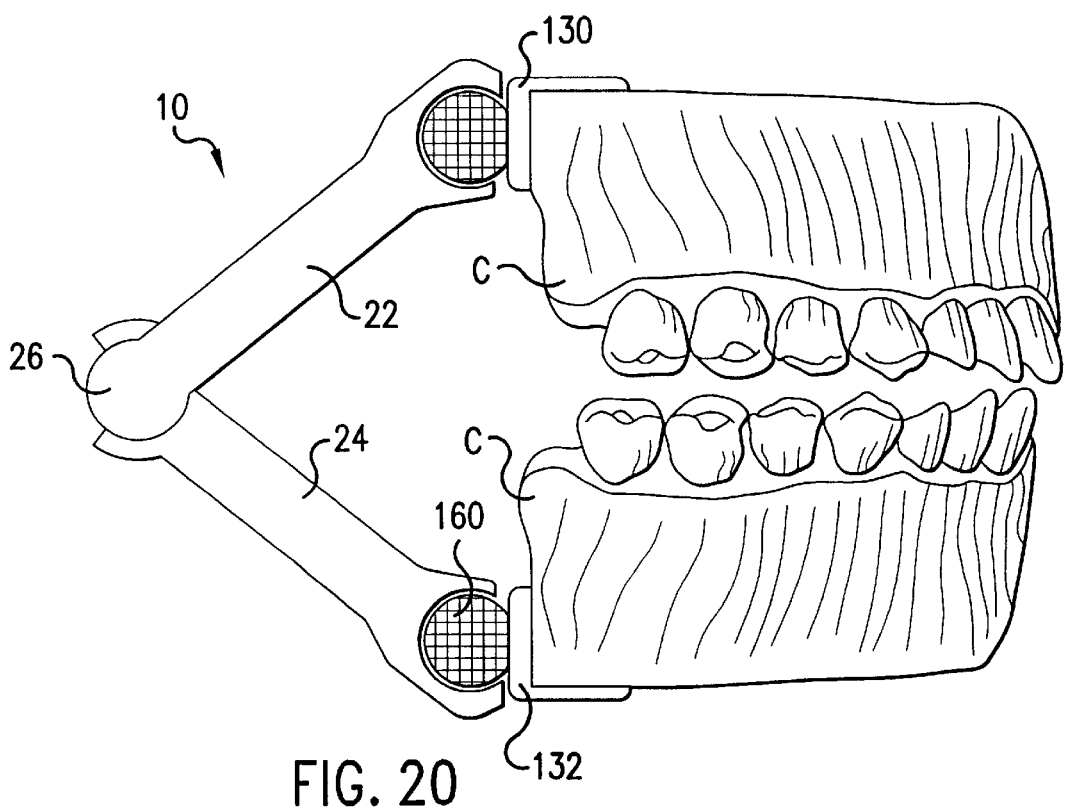
FIG. 20 is a side view of the dental articulator shown in FIG. 19 with dental casts attached thereto.
Figure 21:
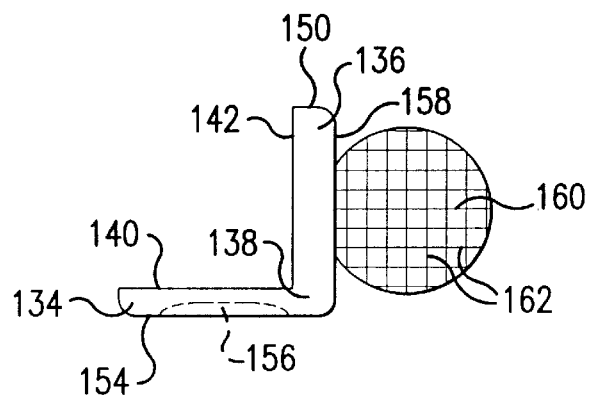
FIG. 21 is a side view of the support shown in FIG. 19.
Figure 22:
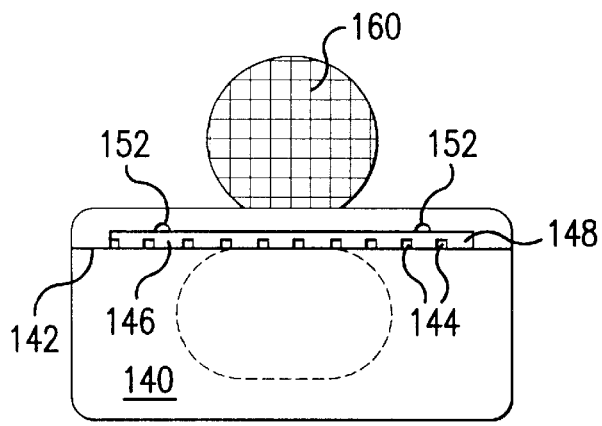
FIG. 22 is a top view of the support shown in FIG. 21.
Figure 23:
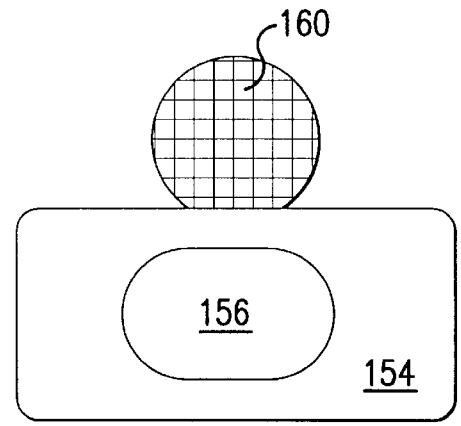
FIG. 23 is a bottom view of the support shown in FIG. 21.
Figure 24:
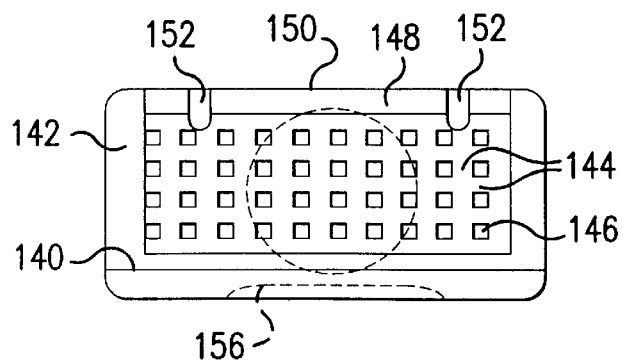
FIG. 24 is a front end view of the support shown in FIG. 21.
Figure 25:
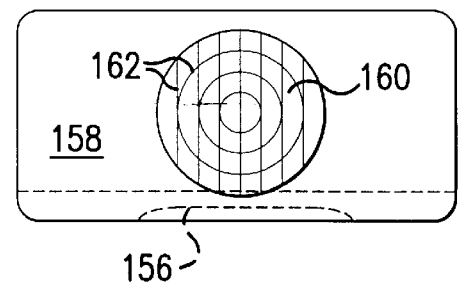
FIG. 25 is a rear end view of the support shown in FIG. 21.

Referring now to FIGS. 19–25, a third embodiment of the dental modeling system will now be described in detail. As shown in FIG. 19, a first articulator arm 22 is pivotally attached to a second articulator arm 24. The articulator arms 22, 24 are the same as those shown in the embodiment of FIG. 1. However, the upper support 12 and the lower support 14 of the FIG. 1 embodiment have been replaced by an upper support 130 and a lower support 132 in the FIG. 19 embodiment. The upper support 130 is identical to the lower support 132, and a discussion will be made with respect to the lower support 132 with the understanding that the same discussion applies to the upper support 130. The lower support 132 includes a bottom member 134 and a back member 136 which together form an L-shaped main body 138. The bottom member has an inner surface 140, and the back member 136 has an inner surface 142 which together receive a dental cast C thereon. The inner surface 140 and the inner surface 142 are oriented at approximately 90° with respect to one another. This allows a dental cast C which typically contains a bottom wall and rear wall which meet at a 90° angle to be properly secured to the main body 138.

The inner surface 142 of the back member 136 includes a glue mesh arrangement formed by a plurality of intersecting grooves 144 which extend into the inner surface 142, thus forming a plurality of raised projections 146 between adjacent intersecting grooves 144. A glue slot 148 is located at the intersection of the inner surface 142 and a top wall 150 of the back member 136. Also, a plurality of glue holes 152 are arranged along the top wall 150 which communicate with the glue slot 148.

To secure the dental cast C to the main body 138, the base of the dental cast C is placed against the bottom member 134 and the back member 136. Glue may then be applied into the glue holes 152 and the glue slot 148, which then passes into the intersecting grooves 144 by capillary or wicking action, which thereby provides a large surface area of glue contact between the back member 136 and the dental cast C.

The inside surface 140 of the bottom member 134 is generally flat. However, it is envisioned that the inside surface 140 may also include a glue mesh arrangement as does the inner surface 142 of the back member.

The bottom member 134 includes an outer surface 154 which includes a depression 156 therein. The depression 156 is similar to the depression 56 of the articulator arms 22, 24. The depression 156 provides a convenient resting point for the finger or thumb of a technician applying glue to the interface between the dental cast C and the main body 138.

The back member 136 includes an outer surface 158 which includes an attachment ball 160 thereon. The attachment ball 160 is similar to the attachment ball 88 shown in FIG. 7. The attachment ball 160 includes a plurality of grooves 162 which are similar to the grooves 90 in the attachment ball 88. The discussion set forth previously with respect to the attachment ball 88 and the grooves 90 is equally applicable to the attachment ball 160 and the grooves 162 of the lower support 132. The grooves 162 form a glue mesh arrangement as described previously.

The lower support 132 is attached to the second articulator arm 24 by gluing the attachment ball 160 to the socket member 54 in the manner described above with respect to the lower support 14. Further, although not shown in the drawings, it should be understood that the lower support 132 and/or the upper support 130 may be formed as an extension of the articulator arms 24, 22 respectively, in the same manner as that shown in the embodiment of FIGS. 12 and 13. Further, it may be desirable to configure the articulator arms 22, 24 with an upper support 12 and a lower support 132. This may occur, for example, when the dental technician already has a lower dental cast C formed, but needs only to pour and form a mating upper dental cast C utilizing the upper support 12.

Referring now to FIGS. 26 and 27, a full arch support 170 is shown. The full arch support 170 includes a row of registration pins 172, two rows of holes 174, a first groove 176 and a second groove 178 which essentially correspond to the registration pins 70, the holes 72, the first groove 74 and the second groove 76 described above with respect to FIG. 7. The full arch support 170 has a rear wall 180 including a cross-member 182 attached thereto. The cross-member 182 provides an attachment point for an articulator arm 184. The articulator arm 184 is essentially the same as the articulator arm 22, except that no socket member is required since the articulator arm 184 is directly attached to the cross-member 182. However, it should be understood that an articulator arm identical to the second articulator arm 24 may be utilized with the full arch support 170, provided that a compatible attachment ball is provided on the cross-member 182 which would then be glued in place in the manner described previously. The full arch support 170 includes a cavity 186, as shown in FIG. 27. Although not shown in the drawings, an auxiliary base member such as that shown in FIG. 14 may be utilized with the full arch support 170 shown in FIG. 26, provided that it is shaped in the full arch manner.

In the present invention, because the registration pins 70 provide sufficient registration of the dental cast C with respect to the main body 16, it is not essential that additional pins be embedded into the dental cast which would be inserted into the holes 72. This is beneficial, for example, in the instance where ceramic crowns are being formed. To make a ceramic crown, the segmented portion of the dental cast having the crown material thereon is placed in a refractory oven at a temperature of approximately 1400°

Fahrenheit. At this temperature, pins formed of standard metals will melt, and therefore it is necessary to use refractory pins which are very expensive. Therefore, because the present invention may be practiced without the utilization of additional pins, it is possible to form ceramic crowns without requiring the added expense of utilizing refractory pins.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A dental modeling system comprising:
   a support for a dental cast, said support including:
      a back member having an inner surface and an outer surface, said inner surface of said back member including:
         a plurality of vertical glue-receiving grooves therein;
         a plurality of non-vertical glue-receiving grooves therein which intersect with said vertical glue-receiving grooves to form a plurality of raised projections between adjacent intersecting vertical and non-vertical glue-receiving grooves; and
         a horizontal glue slot located in an upper edge of said inner surface of said back member and interconnecting with said plurality of vertical glue-receiving grooves; and
      a bottom member having an inner surface and an outer surface, said back member and said bottom member together forming an L-shaped main body with said back member being oriented at approximately 90 degrees with respect to said bottom member.

2. The dental modeling system according to claim 1, wherein said outer surface of said bottom member includes a finger-receiving depression therein.

3. The dental modeling system according to claim 1, wherein said outer surface of said back member includes an attachment member fixed thereto.

4. The dental modeling system according to claim 3, wherein said attachment member is a part-spherical ball.

5. The dental modeling system according to claim 1, further comprising an articulator, said articulator comprising:
   a first articulator arm having a first end and a second end, said first end including a first hinge portion;
   a second articulator arm having a first end and a second end, said first end including a second hinge portion, said second hinge portion of said second articulator arm being pivotally connected to said first hinge portion of said first articulator arm;
   said support being a first support attached to said second end of said first articulator arm for supporting a first dental cast; and
   a second support attached to said second end of said second articulator arm for supporting a second dental cast.

6. The dental modeling system according to claim 1, wherein said non-vertical glue-receiving grooves are horizontal.

7. A dental modeling system comprising:
   a support for a dental cast, said support including:
      a back member having an inner surface and an outer surface, said inner surface of said back member including a plurality of intersecting glue-receiving grooves therein; and
      a bottom member having an inner surface and an outer surface, said back member and said bottom member together forming an L-shaped main body with said back member being oriented at approximately 90 degrees with respect to said bottom member; and
   an articulator, said articulator comprising:
      a first articulator arm having a first end and a second end, said first end including a first hinge portion;
      a second articulator arm having a first end and a second end, said first end including a second hinge portion, said second hinge portion of said second articulator arm being pivotally connected to said first hinge portion of said first articulator arm;
      said support being a first support attached to said second end of said first articulator arm for supporting a first dental cast; and
      a second support attached to said second end of said second articulator arm for supporting a second dental cast,
      wherein said second ends of said first and second articulator arms include an elongated part-cylindrical concave socket member.

8. The dental modeling system according to claim 7, wherein said socket member includes a glue slot therein.

9. The dental modeling system according to claim 7, wherein each of said first and second articulator arms comprise:
   first and second spaced-apart parallel arm members; and
   a cross member interconnecting said arm members together adjacent said hinge portion.

10. The dental modeling system according to claim 9, wherein each of said hinge portions comprise:
    a first finger extending from said cross member adjacent said first arm member; and
    a pair of spaced-apart second fingers extending from said cross member adjacent said second arm member,
    wherein said first finger of said first articulator arm is locatable between said second fingers of said second articulator arm, and said first finger of said second articulator arm is locatable between said second fingers of said first articulator arm.

11. The dental modeling system according to claim 10, wherein each of said second fingers includes a projection thereon, and each of said first fingers include a pair of dimples therein for receiving said projections therein, said first and second articulator arms being pivotal about an axis extending through said projections and said dimples.

12. The dental modeling system according to claim 10, wherein end portions of said first and second fingers are partially circular and received in correspondingly shaped partially circular recesses in said cross members.

13. The dental modeling system according to claim 9, wherein said first and second articulator arms each include a stop portion which are engaged with one another when said first and second articulator arms are pivoted to a predetermined closed position.

14. The dental modeling system according to claim 7, wherein said outer surface of said back member includes an attachment member fixed thereto, said attachment member comprising a part-spherical ball.

15. The dental modeling system according to claim 14, wherein said part-spherical ball is receivable within said elongated part-cylindrical concave socket member of one of said articulator arms.

16. The dental modeling system according to claim 7, wherein said first articulator arm and said second articulator arm are pivotal with respect to one another about a pivot axis defined by said first and second hinge portions, and wherein said support includes an attachment member fixed thereto, said attachment member being receivable within said elongated part-cylindrical concave socket member of one of said articulator arms and shiftable along said elongated part-cylindrical concave socket member in a direction substantially parallel to said pivot axis.

17. The dental modeling system according to claim 7, wherein said plurality of intersecting glue-receiving grooves includes:

a plurality of vertical glue-receiving grooves; and a plurality of non-vertical glue-receiving grooves therein which intersect with said vertical glue-receiving grooves to form a plurality of raised projections between adjacent intersecting vertical and non-vertical glue-receiving grooves.

18. The dental modeling system according to claim 17, further comprising a horizontal glue slot located in an upper edge of said inner surface of said back member and interconnecting with said plurality of vertical glue-receiving grooves.

19. The dental modeling system according to claim 17, wherein said non-vertical glue-receiving grooves are horizontal.

* * * * *